United States Patent [19]
Brandes et al.

[11] Patent Number: 5,059,617
[45] Date of Patent: Oct. 22, 1991

[54] SYNERGISTIC FUNGICIDAL COMPOSITIONS

[75] Inventors: Wilhelm Brandes, Leichlinggen; Helmut Kaspers, Leverkusen; Paul Reinecke, Leverkusen; Hans Scheinpflug, Leverkusen; Wolfgang Krämer, Wuppertal, all of Fed. Rep. of Germany

[73] Assignee: Bayer Aktiengesellschaft, Leverkusen, Fed. Rep. of Germany

[21] Appl. No.: 423,162

[22] Filed: Oct. 18, 1989

Related U.S. Application Data

[60] Division of Ser. No. 936,416, Dec. 1, 1986, Pat. No. 4,902,704, which is a division of Ser. No. 750,719, Jun. 28, 1985, abandoned, which is a continuation of Ser. No. 526,933, Aug. 26, 1983, abandoned.

[30] Foreign Application Priority Data

Sep. 18, 1982 [DE] Fed. Rep. of Germany ....... 3234624

[51] Int. Cl.$^5$ .................. A61K 31/41; A61K 31/12
[52] U.S. Cl. .................. 514/383; 514/634
[58] Field of Search .................. 514/383, 634

[56] References Cited

U.S. PATENT DOCUMENTS

| 4,156,001 | 5/1979 | Brandes et al. | 514/386 |
| 4,661,503 | 4/1987 | Marten et al. | 514/372 |
| 4,888,349 | 12/1989 | Brandes | 514/383 |
| 4,902,704 | 2/1990 | Brandes | 514/383 |

OTHER PUBLICATIONS

Weeds, Calculating Synergistic and Antagonistic Responses of Herbicide Combinations; S. R. Colby, 15, 20–22 (1967).

*Primary Examiner*—Frederick E. Waddell
*Assistant Examiner*—T. Criares
*Attorney, Agent, or Firm*—Sprung, Horn, Kramer & Woods

[57] ABSTRACT

A synergistic fungicidal composition comprising a fungicidally effective amount of (I) a 1,2,4-triazolylalkonol of the formula

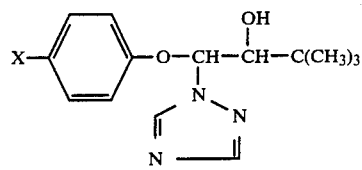

in which
X is chlorine or phenyl plus (II) at least one member selected from the group consisting of
(A) a salt of a heavy metal,
(B) a guanidine or derivative, and
(C) a polyhalogenoalkylthio derivative of the formula

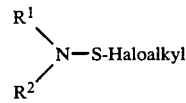

in which
$R^1$ is amidosulphonyl or dimethylamidosulphonyl,
$R^2$ is phenyl, methylphenyl or halogeno phenyl, or
$R^1$ and $R^2$ together are

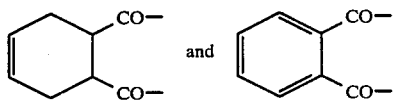

Haloalkyl is alkyl which has up to 2 carbon atoms and is substituted by 2 to 5 halogen atoms.

2 Claims, No Drawings

SYNERGISTIC FUNGICIDAL COMPOSITIONS

This is a division of application Ser. No. 936,416, filed Dec. 1, 1986, now U.S. Pat. No. 4,902,704 which is a division of Ser. No. 750,719, filed June 28, 1985, now abandoned, which is a continuation of application Ser. No. 526,933, filed Aug. 26, 1983, now abandoned.

The present invention relates to new fungicidal active compound combinations of special known 1,2,4-triazolyl-alkanols and other known fungicidal active compounds.

It is already generally known that mixtures containing 1,2,4-triazole derivatives, such as, for example, 1-(4-chlorophenoxy)-3,3-dimethyl-1-(1,2,4-triazol-1-yl) butan-2-one, in combination with other known fungicides exhibit a substantially higher action than the individual components. See U.S. Ser. No. 307,336 filed Sept. 30, 1981, now pending. However, the activity of these active compound mixtures is not always completely satisfactory in all fields of use.

It has now been found that new active compound combinations of special 1,2,4-triazolyt-alkanols of the formula

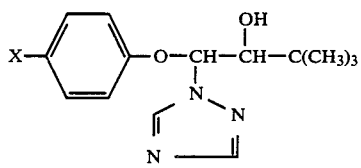

in which X represents chlorine or phenyl, and
(A) salts of heavy metals and/or
(B) guanidine derivatives and/or
(c) polyhalogenoalkylthio derivatives of the general formula

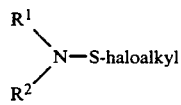

in which
R$^1$ represents amidosulphonyl or dimethylaminosulphonyl,
R$^2$ represents phenyl, methylphenyl or halogenophenyl, or
R$^1$ and R$^2$ together represent the radical

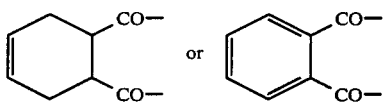

and "haloalkyl" represents alkyl which has up to 2 carbon atoms and is substituted by 2 to 5 halogen atoms,
possess particularly high fungicidal activity.

Surprisingly, the fungicidal action of the active compound combinations according to the invention is substantially higher than the action of the individual components and, where relevant, also than the sum of the individual components (synergistic effect). The discovery of these combinations of special 1,2,4-triazolylalkanols of the formula (I) and of the active compounds of group (A) or (B) and/or (C) given above represents a valuable enrichment of the art.

Formula (I) above gives an unambiguous definition of the 1,2,4-triazolyl-alkanols especially to be used for the combination according to the invention; this formula embraces the two compounds (Ia): X=CL; common name TRIADIMENOL
(Ib): X=

;

common name BITERTANOL.

The stated compounds are generally known (in this context, see German Patent Specifications 2,201,063 and 2,324,010, or the corresponding U.S. Pat. Nos. 3,912,752 and 3,952,002).

If appropriate (A) salts of heavy metals can be used as components of the mixture. Preferably used salts are inorganic copper salts, and copper sulphate and copper chloride, and the corresponding basic salts, such as, for example, copper oxychloride, may be mentioned particularly. The compounds are generally known. Further components from group (A) which can be used as components of the mixture are organo-tin and organo-mercury compounds. Triphenyl-tin acetate (common name FENTIN ACETATE) and methoxyethyl-mercury silicate may be preferably mentioned in this context. These compounds, too, are generally known (in this context, see, for example, the data in R. Wegler, "Chemie der Pflanzenschutz- und Schädlings-bekämpfungs-mittel" [Chemistry of Plant Protection Agents and Pest-Combating Agents], Volume 2, pages 149 and 144, Springer-Verlag, Berlin/Heidelberg/New York, 1970).

If appropriate, (B) guanidine derivatives can also be used as components of the mixture. Dodecylguanidine acetate (common name DODINE) may be particularly mentioned in this context: this compound, too, has long been known (in this context, see R. Wegler, loc. cit., page 70).

Formula (II) gives a definition of the polyhalogenoalkylthio derivatives (group C) which are then to be used, if appropriate, as components of the mixture. The following compounds may be preferably mentioned in this context:

(IIa): R$^1$=(CH$_3$)$_2$N-SO$_2$, R$^2$=

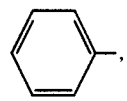, halogenoalkyl=CCl$_2$F (common name DICHLOFLUANID)
(IIb): R$^1$+R$^2$=

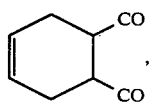, haloalkyl=CCl$_3$ (common name CAPTAN)
(IIc): R$^1$+R$^2$=

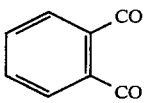

haloalkyl=$CCl_3$ (common name FOLPET)

(IId): $R^1 + R^2 =$

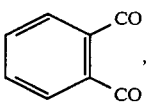

haloalkyl=$CCl_2$—$CHCl_2$ (common name CAPTAFOL)

The compounds have likewise been generally known for a relatively long time (see, for example, R. Wegler, loc. cit., pages 95, 108, 109 and 110).

An active compound combination of the 1,2,4-triazolyl-alkanols of the formula (I) and the active compounds from the groups (A) or (B) and/or (C) can also contain further active compounds (for example as a third component).

The weight ratios of the active compound groups in the active compound combinations can vary within relatively wide ranges. In general, 0.1 to 500 parts by weight of active compound from the active compound classes (A) to (C), preferably from 0.2 to 200 parts by weight, of the latter, particularly preferably 0.5 to 50 parts by weight, are employed per part by weight of 1,2,4-triazolyl-alkanol of the formula (I).

The active compound combinations according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

The active compound combinations according to the invention have a very broad spectrum of action and can be used against parasitic fungi which infest the above-ground parts of plants of attack the plants from the soil, and against seed-borne pathogens. Such active compound combinations possess particular practical importance as seed dressings against phytopathogenic fungi which are borne by the seed, or occur in the soil and attack the crop plants from there. These include seedling diseases, root rots, stalk, haulm, leaf, blossom, fruit and seed diseases which are caused in particular by Tilletia, Urocystis, Ustilago, Septoria, Typhula, Rhynchosporium, Helminthosporium and Fusarium species. As a result of the systemic action of one of the components of the mixture, the plants are also often protected, for a relatively long time after dressing, from pathogens which can attack various parts of the shoot, for example powdery mildew fungi and rust fungi. The active compound combinations can, in addition, also be employed as soil-treatment agents against phytopathogenic fungi, and are active against root rots and tracheomycoses which are caused, for example, by pathogens of the genera Pythium, Verticillium, Phialophora, Rhizoctonia, Fusarjum and Thielaviopsis.

However, the active compound combinations according to the invention also exhibit an outstanding action, when applied directly onto the above-ground parts of plants, against pathogens on various crop plants, such as powdery mildew fungi (Erysiphe, Uncinula, Sphaerotheca and Podosphaera species, *Leveillula taurica*), rust fungi, Venturia species, Cercospora species, Alternaria species, Botrytis species, Phytophthora species, Peronospora species, *Pyricularia oryzae* and *Pellicularia sasakii.*

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is emulsifying agents and/or dispersing agents, and/or foam-forming agents. In the case of the use of water as an extender, organic solvents cam, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl, sulphonates as well as albumin hydrolysation products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs and azole metal phthalocyanine dyestuffs, and trace nutrients such as salts of iron, manganese, boron, copper, cobalt, molybdenum and zinc.

The formulations in general contain between 0.1 and 95% by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02%, are required at the place of action.

The use examples which follow serve as an illustration. Examples of active compounds to be used in active compound combinations according to the invention are listed below:

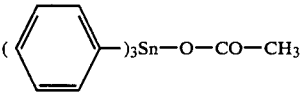

| Active compound No. | Formula | Common name | Reference |
|---|---|---|---|
| 1 | Ia | TRIADIMENOL | DE-QS [German Published Specification] 2,324,010 U.S. Patent Specification 3,952,002 |
| 2 | Ib | BITERTANOL | as in the case of compound 1 |
| 3 | $CuSO_3 \cdot 5H_2O$ | (copper sulphate) | Wegler, loc. cit., page 46 |
| 4 | $3Cu(OH)_2 \cdot CuCl_2 \cdot xH_2O$ | (copper oxychloride) | Wegler, loc. cit., page 47 |
| 5 | $(C_6H_5-)_3Sn-O-CO-CH_3$ | FENTIN ACETATE | Wegler, loc. cit. page 149 |
| 6 | $CH_3-O-C_2H_4-Hg$ silicate | — | Wegler, loc. cit. page 144 |
| 7 | $[n\text{-}C_{12}H_{25}-NH-\overset{NH}{\underset{\|}{C}}-NH_3]^{\oplus} [CH_3-COO]^{(-)}$ | DODINE | Wegler, loc. cit. page 70 |
| 8 | IIa | DICHLOFLUANID | Wegler, loc. cit. page 95 |
| 9 | IIb | CAPTAN | Wegler, loc. cit. page 108 |
| 10 | IIc | FOLPET | Wegler, loc. cit. page 109 |
| 11 | IId | CAPTAFOL | Wegler, loc. cit. page 110 |

EXAMPLE A

Venturia test (apple)/protective

Solvent: 4.7 parts by weight of acetone

Emulsifier: 0.3 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (*Venturia inaequalis*) and then remain in an incubation cabinet at 20° C. and 100% relative atmospheric humidity for 1 day.

The plants are then placed in a greenhouse at 20° C. and a relative atmospheric humidity of about 70%.

Evaluation is carried out 12 days after the inoculation.

TABLE 1

| Venturia test (apple)/protective | | |
|---|---|---|
| Active compound | Infestation in % at an active compound concentration of | |
| 2 (BITERTANOL) (known) | 0.0001% | 44 |
| 5 (FENTIN ACETATE) (known) | 0.0001% | 62 |
| 4 (copper oxychloride) (known) | 0.0005% | 63 |
| Mixture of 2 and 5 (Mixing ratio 1:1) | 0.0001% + 0.0001% | 10 |
| Mixture of 2 and 4 (Mixing ratio 1:5) | 0.0001% + 0.0005% | 22 |

EXAMPLE B

Venturia test (apple)/curative
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for curative activity, young plants are inoculated with an aqueous conidia suspension of the apple scab causative organism (*Venturia inaequalis*). The plants remain in an incubation cabin at 20° C. and 100% relative atmospheric humidity for 1 day and are then placed in a greenhouse. After a given number of hours, the plants are sprayed with the preparation of active compound until dripping wet.

The plants are then placed in a greenhouse at 20° C. and a relative atmospheric humidity of about 70%.

Evaluation is carried out 12 days after the inoculation.

TABLE B

| Venturia test (apple)/curative 42 hours | | |
|---|---|---|
| Active compound | Infestation in % at an active compound concentration of | |
| 2 (BITERTANOL) (known) | 0.00006% | 70 |
| 7 (DODINE) (known) | 0.0003% | 89 |
| Mixture of 2 and 7 (Mixing ratio 1:5) | 0.00006% + 0.0003% | 35 |

EXAMPLE C

*Septoria nodorum* Test (Wheat)/Seed Treatment

The active compounds are used as dry dressings. These are prepared by extending the particular active compound with a ground mineral to give a finely pulverulent mixture, which ensures uniform distribution on the seed surface.

To apply the dressing, the infected seed is shaken with the dressing in a closed glass flask for 3 minutes.

2 batches of 100 grains of the wheat are sown 1 cm deep in standard soil and are cultivated in a greenhouse at a temperature of about 15° C., in seedboxes which are exposed to light for 15 hours daily.

About 3 weeks after sowing, the plants are evaluated for symptoms of septoriosis.

TABLE C

| Septoria nodorum test (wheat)/seed treatment | | |
|---|---|---|
| Active compound | Amount of active compound applied in mg/kg of seed | Diseased plants in % of the total plants which have emerged |
| Not dressed | — | 99.4 |
| 1 (TRIADIMENOL) (known) | 200 | 23.7 |
| 2 (BITERTANOL) (known) | 200 | 46.2 |
| 6 (methoxyethyl-mercury silicate (known) | 17.5 hg+ | 80.2 |
| Mixture of 1 and 6 | 200 + 17.5 Hg+ | 6.7 |
| Mixture of 2 and 6 | 200 + 17.5 Hg+ | 7.7 |

+Comment: As is usual in the case of all mercury-containing plant protection agents, the use amounts given are relative to mg of mercury metal.

EXAMPLE D

*Fusarium eulmorum* Test (Wheat)/Seed Treatment

The active compounds are used as dry dressings. These are prepared by extending the particular active compound with a ground mineral to give a finely pulverulent mixture, which ensures uniform distribution on the seed surface.

To apply the dressing, the infected seed is shaken with the dressing in a closed glass flask for 3 minutes.

2 batches of 100 grains of the wheat are sown 1 cm deep in standard soil and are cultivated in a greenhouse at a temperature of about 18° C., in seedboxes which are exposed to light for 15 hours daily.

About 3 weeks after sowing, the plants are evaluated for symptoms.

TABLE D

| Fusarium culmorum test (wheat)/seed treatment | | |
|---|---|---|
| Active compound | Amount of active compound applied in mg/kg of seed | Diseased plants in % of the total plants which have emerged |
| Not dressed | — | 31.5 |
| 1 (TRIADIMENOL) (known) | 200 | 26.5 |
| 4 (copper oxychloride) (known) | 100 | 28.0 |
| Mixture of 1 and 4 (Mixing ratio 1:0.5) | 200 + 100 | 17.0 |

It is understood that the specification and examples are illustrative but not limitative of the present invention and that other embodiments within the spirit and scope of the invention will suggest themselves to those skilled in the art.

We claim:

1. A fungicidal composition comprising a fungicidally effective amount of (I) a 1,2,4-triazolyl-alkanol of the formula $$X-\text{C}_6\text{H}_4-\text{O}-\text{CH}-\underset{\underset{\text{triazolyl}}{|}}{\text{CH}}-\text{C}(\text{CH}_3)_3$$

with OH on the second carbon in which X is chlorine or phenyl, and (II) n-dodecyl-guanidine acetate of the formula
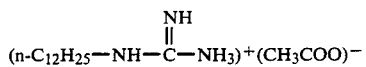
wherein the weight ratio of I:II is between about 1:5.
2. A method of combating fungi which comprises administering to such fungi or to a fungus habitat a fungicidally effective amount of a composition according to claim 1.
* * * * *